United States Patent [19]

George et al.

[11] Patent Number: 5,512,590

[45] Date of Patent: Apr. 30, 1996

[54] 5,6-DIHYDRO-4H-IMIDAZO[2',1':2,3]-IMIDAZO-[4,5,1-IJ]QUINOLINE AND 4,5-DIHYDROIMIDAZO-[1,2-A]PYROLO-[1,2,3-CD]BENZIMIDAZOLE DERIVATIVES, THEIR PREPARATION AND APPLICATION IN THERAPEUTICS

[75] Inventors: Pascal George, St Arnoult en Yvelines; Mireille Sevrin, Paris; Michel Peynot, L'Hay les Roses, all of France

[73] Assignee: Synthelabo, Le Plessis Robinson, France

[21] Appl. No.: 437,053

[22] Filed: May 9, 1995

[30] Foreign Application Priority Data

May 10, 1994 [FR] France ................. 94 05715

[51] Int. Cl.⁶ .............. C07D 471/16; C07D 487/16; A61K 31/415; A61K 31/435
[52] U.S. Cl. ............ 514/394; 514/287; 546/64; 548/301.7
[58] Field of Search .......... 546/64; 548/301.7; 514/287, 394

[56] References Cited

FOREIGN PATENT DOCUMENTS 2593817  8/1987  France .

Primary Examiner—Johann Richter
Assistant Examiner—Laura L. Stockton
Attorney, Agent, or Firm—Jacobson, Price, Holman & Stern

[57] ABSTRACT

The invention discloses compounds formula (I)

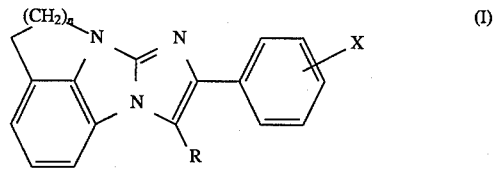

in which n represents the number 1 or 2, X represents a hydrogen atom or indicates that the phenyl ring to which it is attached is substituted by one or two substituents independently chosen from halogen, $C_1$–$C_3$ alkyl, $C_1$–$C_3$ alkoxy and hydroxyl, and R represents a hydrogen atom, a group of formula —$CH_2$—$CO_2$—$R_1$ (in which $R_1$ represents a hydrogen atom or a $C_1$–$C_6$ alkyl group) or a group of formula —$CH_2$—CO—$NR_2R_3$ (in which each of $R_2$ and $R_3$ is independently a hydrogen atom or a $C_1$–$C_3$ alkyl group), or a pharmaceutically acceptable salt thereof, processes for their preparation and their use in the treatment of disorders of GABAergic transmission.

5 Claims, No Drawings

5,6-DIHYDRO-4H-IMIDAZO[2',1':2,3] IMIDAZO-[4,5,1-IJ] QUINOLINE AND 4,5-DIHYDROIMIDAZO-[1,2-A] PYROLO[1,2,3-CD] BENZIMIDAZOLE DERIVATIVES, THEIR PREPARATION AND APPLICATION IN THERAPEUTICS

The present invention provides a compound formula (I)

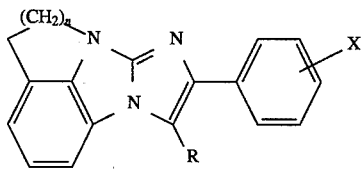

(I)

in which n represents the number 1 or 2,

X represents a hydrogen atom or indicates that the phenyl ring to which it is attached is substituted by one or two substituents independently chosen from halogen, $C_1$–$C_3$ alkyl, $C_1$–$C_3$ alkoxy and hydroxyl, and R represents a hydrogen atom, a group of formula —$CH_2$—$CO_2$—$R_1$ (in which $R_1$ represents a hydrogen atom or a $C_1$–$C_6$ alkyl group), a group of formula —$CH_2$—CO—$NR_2R_3$ (in which each of $R_2$ and $R_3$ is independently a hydrogen atom or a $C_1$–$C_3$ alkyl group) or a pharmaceutically acceptable salt thereof.

Preferred are compounds of formula (I) or pharmaceutically acceptable salts thereof in which n represents the number 1, X represents a fluorine or chlorine atom or a methyl or a methoxy group, and R represents a group of formula —$CH_2$—CO—NH—$CH_3$ or —$CH_2$—CO—N($CH_3$)$_2$.

Particularly preferred is 8-(4-fluorophenyl)-N-methyl-4,5-dihydroimidazo-[1,2-a]pyrrolo[1,2,3-cd]benzimidazole-9-acetamide and its pharmaceutically acceptable salts, for example, hydrogen chloride salts.

In accordance with the invention, the compounds of general formula (I) can be prepared according to a process illustrated by the following scheme.

A derivative of formula (II), in which n is as defined above, is reacted with a 2-halo-1-phenylethanone of formula (III), in which X is as defined above and Hal represents a chlorine or bromine atom, in order to obtain a guanidinium salt of formula (IV), in which n and X are as defined above, which is cyclized by heating, typically at a temperature of 80° to 150° C., in a solvent such as, for example, polyphosphoric acid, in order to obtain a derivative of formula (Ia), which corresponds to the formula (I) when R represents H.

If desired, this derivative of formula (Ia) is then reacted with N,N-dimethylglyox-amide (which can be obtained in situ by hydrolysis of 2,2-diethoxy-N,N-dimethylacetamide in the presence of a strong acid, as described in European Patent Application EP-A-251859), in a protic solvent, such as acetic acid, typically at a temperature of 20° to 80° C., in order to obtain an α-hydroxyacetamide derivative of formula (V), in which n and X are as defined above, which is then treated with a sulphuric or phosphoric acid polyhalide, for example thionyl chloride or phosphorus oxychloride, or any other equivalent agent, in an inert solvent, for example a chlorinated or ethereal solvent such as dichloromethane or tetrahydrofuran, typically at a temperature of 20° to 80° C., in order to form the corresponding α-halo-acetamide derivative, then the latter is reacted either with a reducing agent such as a simple or complex alkali metal hydride, for example sodium or potassium borohydride, in a protic solvent, for example an aliphatic alcohol such as methanol or ethanol, or in a water-miscible inert solvent, for example dioxane or tetrahydrofuran, typically at a temperature of −40° to 40° C., or with a reducing agent such as an alkali metal hyposulphite or dithionite, for example sodium hyposulphite or dithionite, or alternatively with sodium hydroxymethylsulphoxylate (Rongalite®), in an inert solvent, for example a chlorinated solvent such as dichloromethane, optionally in the presence of a water-miscible inert cosolvent, for example N,N-dimethylformamide or N-methylpyrrolidone, typically at a temperature of 20° to 40° C., in order to obtain an N,N-dimethylacetamide derivative of formula (Ib), in which n and X are as defined above, which corresponds to the formula (I) when R represents —$CH_2$—CO—N($CH_3$)$_2$.

Scheme

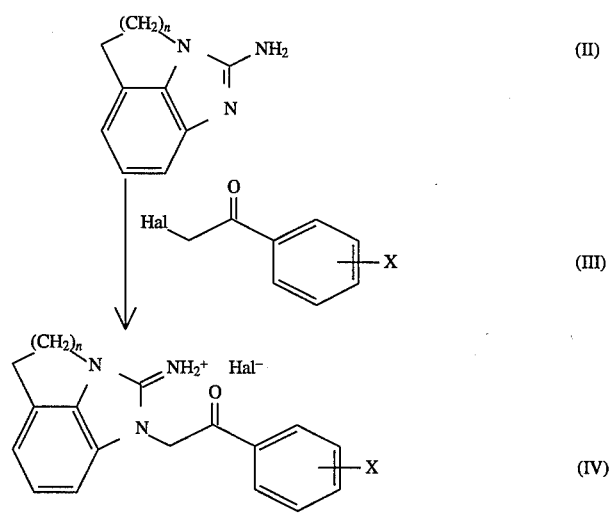

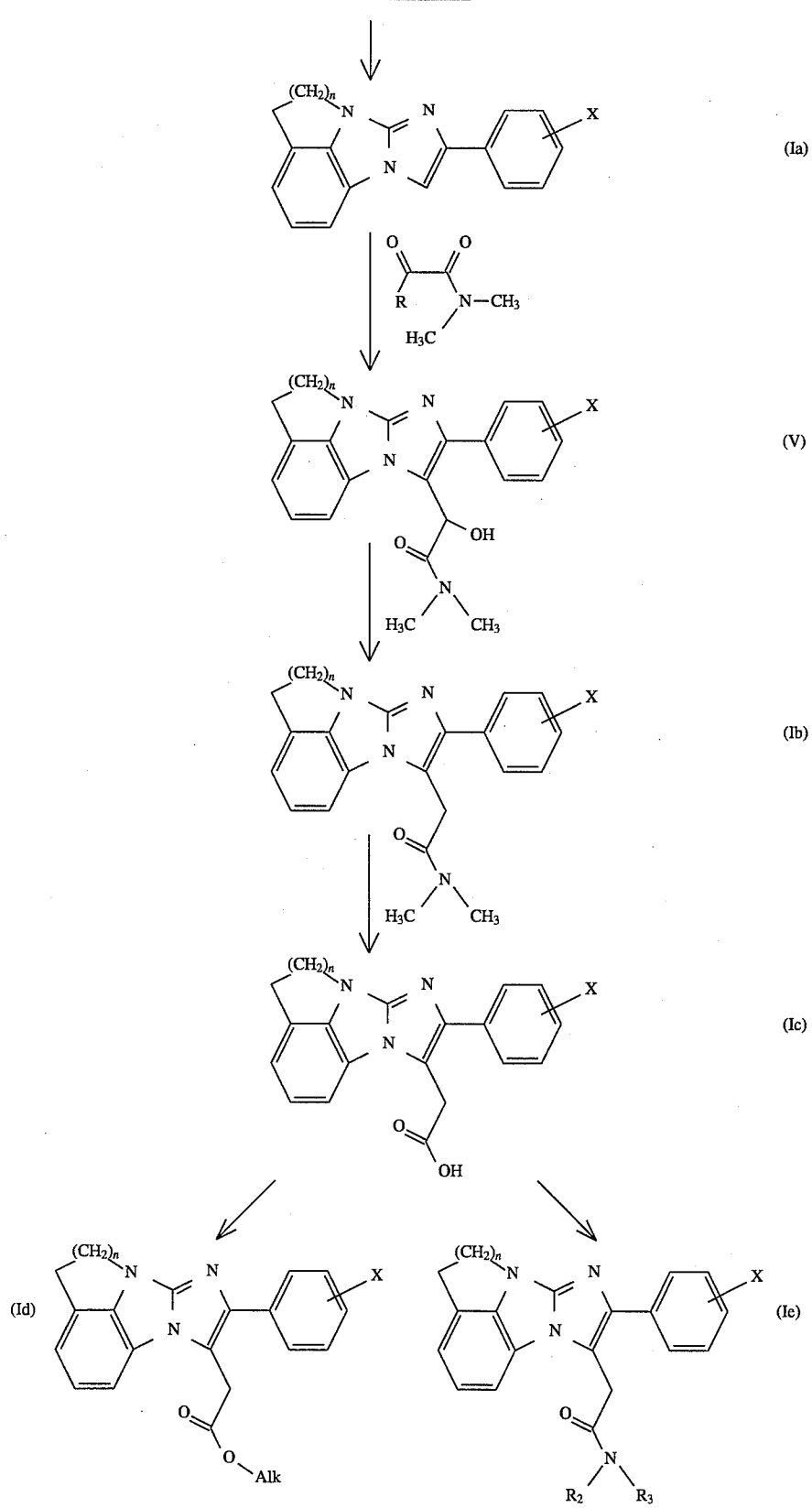
If desired, the compound of formula (Ib) is converted to the acid of formula (Ic), in which n and X are as defined above, by hydrolysis typically by means of a strong base, for example sodium hydroxide or potassium hydroxide, in a protic solvent, for example ethanol or 2-methoxyethanol, in the presence of water.

If desired, the acid of formula (Ic) is finally reacted
either with thionyl chloride, in a $C_1$–$C_6$ aliphatic alcohol, typically at a temperature of 20° to 120° C., in order to obtain an ester of formula (Id), in which Alk represents a $C_1$–$C_6$ alkyl group and n and X are as defined above,
or with N,N'-carbonyldiimidazole, in an inert solvent, for example a chlorinated or ethereal solvent such as dichloromethane or tetrahydrofuran, typically at a temperature of 20° to 50° C., in order to obtain the corresponding imidazolide and the latter is treated with an amine of general formula $HNR_2R_3$, in which $R_2$ and $R_3$ are as defined above, in order to obtain an amide of formula (Ie), in which n, X, $R_2$ and $R_3$ are as defined above, typically at a temperature of 0° to 25° C.

The starting compound of formula (II) in which n represents 1 (that is to say 4,5-dihydropyrrolo[1,2,3-cd]benzimidazol-2-amine) is novel and forms part of the invention; the attempts to synthesize this compound, described in the literature, for example in J. Org. Chem. (1965), 30, 2589, have been fruitless and it has never previously been isolated.

In accordance with the invention, it can be prepared by reacting cyanogen bromide with 2,3-dihydro-1H-indol-7-amine, typically at a temperature of 50° to 70° C., in a protic solvent, for example in water.

The starting compound of formula (II) in which n represents 2 (that is to say 5,6-dihydro-4H-imidazo[4,5,1-ij]quinolin-2-amine) is known and described in the form of the imine tautomer in J. Org. Chem. (1963), 28, 2581. It can be obtained from 1,2,3,4-tetrahydroquinolin-8-amine.

1,2,3,4-Tetrahydroquinolin-8-amine and 2,3-dihydro-1H-indol-7-amine are known and described, for example, in Bull. Soc. Chim. Jpn. (1989), 62, 2968, Heterocycles (1992), 34 (5), 907, J. Org. Chem. (1965), 30, 2589 and J. Pr. Soc. N. S. Wales (1938), 71, 462– 474.

The compounds of formula (III) are either commercially available or are described in the literature and can be prepared according to any known method from the corresponding acetophenones and appropriate halogenating agents.

The examples which will follow illustrate in detail the preparation of several compounds according to the invention.

Elemental microanalyses and the I.R. and N.M.R. spectra confirm the structures of the compounds obtained. The numbers indicated between brackets in the titles of the examples correspond to those of the 1st column of the table given later.

Example 1 (Compound No. 1)

8-Phenyl-4,5-dihydroimidazo[1,2-a]pyrrolo[1,2,3-cd]benzimidazole.

1.1. 1-Acetyl-2,3-dihydro-1H-indol-7-amine.

15 g of 10% palladium-on-charcoal are added to a solution of 37 g (0.13 mol) of 1-acetyl-5-bromo-7-nitro-2,3-dihydro-1H-indole and the suspension is hydrogenated in a Parr apparatus at a pressure of 0.3 MPa and at ambient temperature for 30 min.

The catalyst is removed by filtration and the filtrate is concentrated under reduced pressure. The residue is dissolved in 500 ml of water and treated with an excess of sodium carbonate to basic pH. The insoluble material is collected by filtration, washed with water and dried. 20.3 g of product are obtained.

Melting point: 159° C.

1.2. 2,3-Dihydro-1H-indol-7-amine.

A solution of 20 g (0.113 mol) of 1-acetyl-2,3-dihydro-1H-indol-7-amine in 80 ml of 1N hydrochloric acid is heated at reflux for 1 h. It is cooled to ambient temperature and treated with an excess of aqueous ammonia to a pH of approximately 8 and is then treated with 3 times 100 ml of ether. The organic phases are combined, dried over magnesium sulphate and filtered and the solvent evaporated under reduced pressure. The oily residue is distilled, boiling point: 150°–160° C. at 133 Pa (1 mmHg). 13 g of oily product are obtained.

1.3. 4,5-Dihydropyrrolo[1,2,3-cd]benzimidazol-2-amine.

10 g (0.094 mol) of cyanogen bromide are added, in small portions, to a solution of 10.5 g (0.078 mol) of 2,3-dihydro-1H-indol-7-amine in 200 ml of water while maintaining the temperature of the reaction mixture at 60° C. After cooling to ambient temperature, sodium carbonate is added until saturation. The insoluble material is collected by filtration, dried and purified by chromatography on a column of silica gel, elution being carried out with methanol. The purified fraction is recrystallized from toluene. 3.35 g of product are obtained.

Melting point: 225°–226° C.

1.4. N-[1-(2-Oxo-2-phenylethyl)-4,5-dihydropyrrolo[1,2,3-cd]benzimidazol-2(1H)-ylidene]iminium bromide.

A solution of 3.2 g (0.02 mol) of 4,5-dihydropyrrolo[1,2,3-cd]benzimidazol-2-amine and 4 g (0.02 mol) of 2-bromo-1-phenylethanone in 350 ml of absolute ethanol is stirred for 4 h at a temperature of 80° C. and then 12 h at ambient temperature. The insoluble material is collected by filtration and dried. 6.5 g of salt are obtained, which salt is used as is in the following stage.

Melting point>270° C.

1.5. 8-Phenyl-4,5-dihydroimidazo[1,2-a]pyrrolo[1,2,3-cd]benzimidazole.

A mixture of 4.4 g (0.0123 mol) of N-[1-(2-oxo-2-phenylethyl)-4,5-dihydropyrrolo[1,2,3-cd] benzimidazol-2(1H))-ylidene]iminium bromide and 50 g of 84% polyphosphoric acid is heated for 3 h at 120° C. with stirring. The mixture is then treated, at ambient temperature, with a mixture of water and ice (500 ml and 500 g) and is then neutralized with 30% sodium hydroxide solution. The insoluble material is collected by filtration, washed with water and dried at 60° C. 3 g of white product are obtained, which product is purified by chromatography on a column of silica gel, elution being carried out with a 97/3 dichloromethane/acetone mixture. The purified fraction is evaporated under reduced pressure and the residue is recrystallized from toluene, washed with pentane and dried. 2.3 g of white product are obtained.

Melting point: 192°–193° C.

Example 2 (Compound No. 2)

N,N-Dimethyl-8-phenyl-4,5-dihydroimidazo[1,2-a]pyrrolo[1,2,3-cd]benzimidazole-9-acetamide.

2.1. α-Hydroxy-N,N-dimethyl-8-phenyl-4,5-dihydroimidazo[1,2-a]pyrrolo[1,2,3-cd] benzimidazole-9-acetamide.

5.26 g (0.03 mol) of 2,2-diethoxy-N,N-dimethylacetamide and 0.7 ml of concentrated hydrochloric acid in 50 ml of acetic acid are heated for 1 h 30, under a nitrogen atmosphere, at a temperature of 50° C. 2.5 g (0.03 mol) of sodium acetate are added thereto and heating is carried out for a further 30 min at 50° C. 2.7 g (0.0104 mol) of 8-phenyl-4,5-dihydroimidazo[1,2-a] pyrrolo[1,2,3-cd]benzimidazole are added to this mixture, heating is maintained at 50° C. for 2 h and the reaction mixture is left standing for 18 h.

The mixture is evaporated to dryness at a temperature of less than 50° C. and the residue is treated with 200 ml of water, 200 ml of dichloromethane and an excess of sodium carbonate until the two-phase mixture is neutral.

The organic phase is separated by settling and dried over magnesium sulphate and the solvent is evaporated under reduced pressure. The residue is purified by chromatography on a column of silica gel, elution being carried out with a 95/5 chloroform/acetone mixture. An oily product is obtained which crystallizes by treatment with diethyl ether. After drying, 2.7 g of white product are isolated.

Melting point: 187°–189° C.

2.2. N,N-dimethyl-8-phenyl-4,5-dihydroimidazo[1,2-a]pyrrolo[1,2,3-cd]benzimidazole-9-acetamide.

2.2.1. α-Chloro-N,N-dimethyl-8-phenyl-4,5-dihydroimidazo[1,2-a]pyrrolo[1,2,3-cd]benzimidazole-9-acetamide.

15 g (0.126 mol) of thionyl chloride are added, with stirring, to 2.6 g (0.0072 mol) of α-hydroxy-N,N-dimethyl-8-phenyl-4,5-dihydroimidazo[1,2-a]pyrrolo[1,2,3-cd]benzimidazole-9-acetamide, dissolved in 50 ml of dry dichloromethane. Stirring is maintained for 4 h, under a nitrogen atmosphere, and the reaction mixture is left standing overnight. The mixture is evaporated to dryness, under reduced pressure, and the residue is taken up in toluene and again evaporated. The residue is triturated in diethyl ether, quickly dried and used as is in the following stage.

2.2.2. N,N-Dimethyl-8-phenyl-4,5-dihydroimidazo[1,2-a]pyrrolo[1,2,3-cd]benzimidazole-9-acetamide.

The α-chloro-N,N-dimethyl-8-phenyl-4,5-dihydroimidazo[1,2-a]pyrrolo[1,2,3-cd]benzimidazole-9-acetamide obtained above is dissolved in a mixture of 50 ml of dry dichloromethane and 20 ml of N,N-dimethylformamide. 3.08 g (0.002 mol) of Rongalite® are added to this solution and stirring is carried out for 15 h at ambient temperature.

The solvent is evaporated to dryness, at a temperature of the order of 50° C., and the residue is taken up in a saturated sodium hydrogencarbonate solution. The aqueous phase is treated with dichloromethane, the organic phase is separated and dried over magnesium sulphate and the solvent is evaporated under reduced pressure. The residue is purified by chromatography on a column of silica gel, elution being carried out with a 95/5 dichloromethane/acetone mixture and the purified fraction is recrystallized from isopropyl alcohol and dried at 100° C. under reduced pressure. 0.85 g of solid is obtained.

Melting point: 224°–225° C.

Example 3 (Compound No. 3)

8-Phenyl-4,5-dihydroimidazo[1,2-a]pyrrolo[1,2,3-cd]benzimidazole-9-acetic acid.

A mixture of 0.45 g (0.0013 mol) of N,N-dimethyl-8-phenyl-4,5-dihydroimidazo[1,2-a]pyrrolo[1,2,3-cd]benzimidazole-9-acetamide and 0.28 g of sodium hydroxide (0.007 mol), dissolved in a mixture of 10 ml of 2-methoxyethanol and 2 ml of water, is heated for 6 h at reflux.

The solvents are evaporated under reduced pressure and the residue is taken up in 50 ml of water. An insoluble material is removed by filtration and the filtrate is acidified using acetic acid. The insoluble material is collected by filtration, washed with water to pH 5 and dried at 80° C. under reduced pressure for 8 h. 0.4 g of beige-white solid is obtained.

Melting point: 270°–275° C. (with decomposition).

Example 4 (Compound No. 4)

Methyl 8-phenyl-4,5-dihydroimidazo[1,2-a]pyrrolo[1,2,3-cd]benz-imidazole-9-acetate.

0.2 ml of thionyl chloride are added to a suspension, cooled to 0° C., of 0.02 g of 8-phenyl-4,5-dihydroimidazo-[1,2-a]pyrrolo[1,2,3-cd]benzimidazole-9-acetic acid in 10 ml of methanol and the mixture is left stirring at ambient temperature for 24 h.

The solvent is evaporated under reduced pressure and the residue is taken up in an excess of saturated aqueous sodium hydrogencarbonate solution to pH>7 and extracted with dichloromethane. The organic phase is separated, dried over magnesium sulphate and filtered and the solvent is evaporated under reduced pressure.

The residue is taken up in diisopropyl ether, is allowed to crystallize while cold and 0.015 g of product is obtained.

Melting point: 164°–165° C.

Example 5 (Compound No. 5)

N-Methyl-8-phenyl-4,5-dihydroimidazo[1,2-a]pyrrolo[1,2,3-cd]benzimidazole-9-acetamide.

0.37 g (0.00116 mol) of 8-phenyl-4,5-dihydroimidazo[1,2-a]pyrrolo[1,2,3-cd]benzimidazole-9-acetic acid and 0.23 g (0.0014 mol) of N,N'-carbonyldiimidazole in 15 ml of dry tetrahydrofuran are heated for 4 h at a temperature of 50° C., under a nitrogen atmosphere.

A stream of dry gaseous methylamine is then passed, while cold, into the reaction mixture for 30 min, stirring is carried out for 4 h at ambient temperature and the reaction mixture is left standing overnight. The solvent and the excess amine are evaporated under reduced pressure, the residue is taken up in 30 ml of water and 100 ml of dichloromethane and stirring is carried out for a few minutes. The organic phase is separated and dried over magnesium sulphate and the solvent is evaporated under reduced pressure. The residue is recrystallized from absolute ethanol and the crystals obtained are washed with ether and dried. 0.26 g of solid is obtained.

Melting point: 269°–270° C.

Example 6 (Compound No. 6)

9-Phenyl-5,6-dihydro-4H-imidazo[2',1':2,3]imidazo[4,5,1-ij]quinoline and its hydrochloride.

6.1. 1,2,3,4-Tetrahydroquinolin-8-amine.

80 g (3.5 mol) of sodium are added, in small portions, to a solution, maintained at a temperature of 50° to 60° C., of 45 g (0.312 mol) of quinolin-8-amine in 1 l of absolute ethanol. At the end of the addition, the mixture is heated until the sodium has disappeared and is then cooled with a mixture of water and ice. The reaction mixture is then treated with 200 ml of water and is completely evaporated under reduced pressure.

The solid residue is treated with three times 300 ml of diethyl ether, the organic phases are combined and dried over magnesium sulphate and the solvent is evaporated. The residue is purified by chromatography on a column of silica gel, elution being carried out with a 90/10 to 85/15 dichloromethane/diethyl ether mixture. The purified fraction is evaporated under reduced pressure and the residue dried at 60° C. under vacuum. 30 g of yellow oil are obtained, which oil is used as is in the following stage.

6.2. 5,6-Dihydro-4H-imidazo[4,5,1-ij]quinolin-2-amine.

A solution of 11.1 g (0.105 mol) of cyanogen bromide in 50 ml of methanol is added to a solution, cooled to 0° C., of 14.8 g (0.1 mol) of 1,2,3,4-tetrahydroquinolin-8-amine in 100 ml of methanol. The reaction is exothermic. After stirring for 1 h at ambient temperature and leaving to stand overnight, 100 ml of diethyl ether are added to the mixture and stirring is carried out for 30 min.

The hydrobromide of the expected product is collected by filtration, washed with diethyl ether and superficially dried. It is dissolved in 200 ml of water and 25 ml of 30% sodium hydroxide solution are added, while vigorously stirring the mixture. After stirring for 1 h, the suspension obtained is filtered and the precipitate is washed with water and dried. 13.6 g of solid are obtained.

Melting point: 200° C. (literature: 201°–202° C.).

6.3. N-[1-(2-Oxo-2-phenylethyl)-1,4,5,6-tetrahydro-2H-imidazo[4,5,1 -ij]quinol-2-ylidene]iminium bromide.

13.5 g (0.0779 mol) of 5,6-dihydro-4H-imidazo[4,5,1-ij] quinolin-2-amine and 15.9 g (0.08 mol) of 2-bromo-1-phenylethanone in 1 l of absolute ether are heated for 4 h, under a nitrogen atmosphere, at reflux of the solvent.

After standing overnight, the insoluble material is collected by filtration, washed with ethanol and then with diethyl ether and dried. 21.5 g of the expected salt are obtained.

Melting point>270° C.

6.4. 9-Phenyl-5,6-dihydro-4H-imidazo[2',1':2,3]imidazo[4, 5,1-ij]quinoline and its hydrochloride.

A mixture of 21 g (0.0564 mol) of N-[1-(2-oxo-2-phenylethyl)-1,4,5,6-tetrahydro-2 H-imidazo[4,5,1-ij]quinol-2-ylidene]iminium bromide in 250 g of 84% polyphosphoric acid is heated, with stirring, for 3 h at 120° C.

The still hot (80°–100° C.) mixture is poured into a mixture of 500 ml of water and 500 g of ice, which is kept stirring. The solution is neutralized, while cold, using 30% sodium hydroxide solution. The resulting suspension is filtered and the insoluble material is washed three times with water and dried under reduced pressure. 15 g of product are obtained, which product is purified by chromatography on a column of silica gel, elution being carried out with dichloromethane. 11.5 g of solid are obtained.

Melting point: 103°–104° C.

If desired, it is possible to prepare the hydrochloride from 1 g (0.00366 mol) of base dissolved in 25 ml of absolute ethanol and 3 ml of a 1.5N solution of gaseous hydrochloric acid in dry ethanol. The hydrochloride is recrystallized from a 90/10 2-methoxyethanol/water mixture and the crystals obtained are washed with ethyl alcohol and diethyl ether and dried for 10 h at 100° C. under reduced pressure. 0.8 g of white product is obtained.

Melting point: 295°–300° C. (with decomposition).

Example 7 (Compound No. 7)

N,N-Dimethyl-9-phenyl-5,6-dihydro-4H-imidazo[2',1':2,3]imidazo[ 4,5,1-ij]quinoline-10-acetamide.

7.1. α-Hydroxy-N,N-dimethyl-9-phenyl-5,6-dihydro-4H-imidazo[ 2',1':2,3]imidazo[4,5,1-ij]quinoline-10-acetamide and its hydrochloride.

A mixture of 17.5 g (0.1 mol) of 2,2-diethoxy-N,N-dimethylacetamide, 2 ml of concentrated hydrochloric acid (35%) and 170 ml of glacial acetic acid is heated for 2 h at 50° C. under a nitrogen atmosphere. 8.2 g of anhydrous sodium acetate are then added and the mixture is stirred for 30 min at 50° C. Finally, 9 g (0.0329 mol) of 9-phenyl-5, 6-dihydro-4 H-imidazo[2',1':2,3]imidazo[4,5,1-ij]quinoline are added to this mixture, cooled to 0° C., stirring is carried out for 2 h at ambient temperature and the reaction mixture is left standing overnight. The acetic acid is evaporated under reduced pressure and the residue is taken up in 100 ml of water and 200 ml of dichloromethane. This two-phase mixture, kept vigorously stirring, is treated with sodium carbonate, in small portions, to alkaline pH. The organic phase is separated and dried over sodium sulphate and the solvent is evaporated under reduced pressure. The residue is purified by chromatography on a column of silica gel, elution being carried out with a 95/5 dichloromethane/acetone mixture. The purified fraction is evaporated under reduced pressure and 9.2 g of oil are obtained, which oil is used as is in the following stage.

If desired, it is possible to prepare the hydrochloride from 0.1 g of base and one equivalent of gaseous hydrochloric acid dissolved in diethyl ether. The hydrochloride is recrystallized from acetonitrile and 0.075 g of white solid is obtained.

Melting point: 198°–200° C.

7.2. N,N-Dimethyl-9-phenyl-5,6-dihydro-4H-imidazo[2', 1':2,3]imidazo[4,5,1 -ij]quinoline-10-acetamide.

a) 60 g, i.e. 36.5 ml, of thionyl chloride are added to a solution of 9 g (0.024 mol) of α-hydroxy-N,N-dimethyl-9-phenyl-5,6-dihydro-4H-imidazo[2',1':2,3]imidazo[ 4,5,1-ij]quinoline-10-acetamide in 200 ml of dichloromethane. After stirring for 4 h at ambient temperature and standing overnight, the solvent and the excess thionyl chloride are evaporated under reduced pressure. The residue is taken up in toluene and again evaporated. The hydrochloride is obtained in the form of a gummy product and is used as is in the following stage.

b) The gummy product obtained in the preceding stage is dissolved in a mixture of 200 ml of dry dichloromethane and 150 ml of dry N,N-dimethylformamide, 11.1 g (0.072 mol) of Rongalite® are added thereto and the mixture is stirred for 8 h at ambient temperature.

The solvents are evaporated under reduced pressure, without exceeding a temperature of 50° C., and the residue is taken up in 200 ml of saturated aqueous sodium hydrogencarbonate solution and treated with 200 ml of dichloromethane. The organic phase is separated and dried over sodium sulphate, the solvent is evaporated under reduced pressure and the residue is purified by chromatography on a column of silica gel, elution being carried out with a 97/3 dichloromethane/methanol mixture. The purified fraction is concentrated and the residue is recrystallized from ethyl acetate. The crystals are washed with diethyl ether, dried for 8 h at 100° C. under reduced pressure and 6.4 g of white solid are obtained.

Melting point: 216°–217° C.

Example 8 (Compound No. 8)

9-Phenyl-5,6-dihydro-4H-imidazo[2',1':2,3] imidazo[4,5,1-ij]quinoline-10-acetic acid.

A solution of 6 g of sodium hydroxide in 25 ml of water is added to a solution of 5.5 g (0.0153 mol) of N,N-dimethyl-9-phenyl-5,6-dihydro-4H-imidazo[2',1':2,3]imidazo[ 4 5,1-i3]quinoline-10-acetamide in 150 ml of 2-methoxyethanol and the mixture is brought to reflux of the solvent for 8 h.

The mixture is cooled, the solvent is evaporated under reduced pressure at 60° C. and the residue is taken up in 200 ml of water and treated with 6N hydrochloric acid to a pH of 8.5 to 9. The insoluble material which has formed is removed by filtration, the filtrate is brought to a pH of 3.8 to 4 with dilute hydrochloric acid and the insoluble material is collected by filtration, washed with water and dried at 60°–80° C. under reduced pressure. 4.7 g of solid are obtained.

Melting point: 246°–248° C. (with decomposition).

Example 9 (Compound No. 9)

9-Phenyl-5,6-dihydro-4H-imidazo[2',1':2,3]imidazo[4,5,1-ij]quinoline-10-acetamide.

A mixture of 1.1 g (0.0033 mol) of 9-phenyl-5,6-dihydro-4H-imidazo[ 2',1':2,3]imidazo[4,5,1-ij]quinoline-10-acetic acid and 0.58 g (0.0036 mol) of N,N'-carbonyldiimidazole in 50 ml of dry tetrahydrofuran is heated for 1 h at 50° C., with stirring. The mixture is cooled, treated with a stream of ammonia for 30 min, stirred for 2 h and left standing overnight.

The solvent is evaporated under reduced pressure and the residue is washed with water, then with a saturated aqueous sodium hydrogencarbonate solution, then again with water and finally dried at 100° C. under reduced pressure. It is recrystallized from absolute ethanol and 0.85 g of solid is obtained.

Melting point: 249°–250° C.

Example 10 (Compound No. 10)

N-Methyl-9-phenyl-5,6-dihydro-4H-imidazo[2',1':2,3]imidazo[4,5,1-ij]quinoline-10-acetamide.

The preparation is carried out in the way described in Example 5, from 1.1 g (0.0033 mol) of 9-phenyl-5,6-dihydro-4H-imidazo[ 2',1':2,3]imidazo[4,5,1-ij]quinoline-10-acetic acid with an excess of gaseous methylamine. After crystallization from absolute ethanol, 0.73 g of solid is obtained.

Melting point: 247°–248° C.

Example 11 (Compound No. 11)

Methyl 9-phenyl-5,6-dihydro-4H-imidazo[2',1'L:2,3]imidazo[4,5,1-ij]quinoline- 10-acetate.

0.5 ml of thionyl chloride is added dropwise to a suspension, cooled to 0° C., of 0.5 g (0.0015 mol) of 9-phenyl-5,6-dihydro-4H-imidazo[2',1':2,3]imidazo[4,5,1-ij]quinoline-10-acetic acid in 20 ml of methanol and the mixture is heated at 60° C. and under a dry nitrogen atmosphere for 8 h.

The solvent is evaporated under reduced pressure and the residue is taken up in an excess of saturated aqueous sodium hydrogencarbonate solution to pH>7 and extracted with diethyl ether. The organic phase is separated, dried over magnesium sulphate and filtered and the solvent is evaporated under reduced pressure. The oily residue is taken up in diisopropyl ether, allowed to crystallize while cold and 0.38 g of solid is obtained.

Melting point: 123°–124° C.

Example 12 (Compound No. 16)

8-(4-Fluorophenyl)-4,5-dihydroimidazo[1,2-a]pyrrolo[1,2,3-cd]benzimidazole.

12.1. 2-Bromo-1-(4-fluorophenyl)ethanone.

33.6 g, i.e. 10.8 ml, (0.21 mol) of bromine are added dropwise to a solution of 28 g (0.2 mol) of 1-(4-fluorophenyl)ethanone in 200 ml of chloroform. After 15 min at ambient temperature, 100 ml of water are added, the organic phase is separated, washed with 50 ml of water, dried over magnesium sulphate and filtered, the solvent is evaporated under reduced pressure, the residue is dissolved in 200 ml of pentane at 40° C., the solution is cooled to −5° C. with stirring and the crystals are filtered and dried under reduced pressure. 32.1 g of product are obtained.

Melting point: 47°–48° C.

12.2. N-[1-[2-(4-Fluorophenyl)-2-oxoethyl]-4,5-dihydropyrrolo[ 1,2,3-cd]benzimidazol-2(1H)ylidene]iminium bromide.

A solution of 13 g (0.06 mol) of 2-bromo-1-(4-fluorophenyl)ethanone in 50 ml of ethanol is added to a solution of 9.5 g (0.06 mol) of 4,5-dihydropyrrolo[1,2,3-cd]benzimidazol-2-amine in 450 ml of ethanol, stirring is maintained for 6 h, 500 ml of diethyl ether are added and the mixture is left standing overnight.

The solid is separated by filtration, washed with diethyl ether and dried. 20.7 g of product are obtained.

Melting point: 260°–265° C. (decomposition).

12.3. 8-(4-Fluorophenyl)-4,5-dihydroimidazo[1,2-a]pyrrolo[1,2,3-cd]benzimidazole.

A mixture of 20.5 g (0.0545 mol) of N-[1-(2-(4-fluorophenyl)-2-oxoethyl)-4,5 -dihydropyrrolo[1,2,3-cd]benzimidazol-2(1H)-ylidene]iminium bromide and 200 g of 84% polyphosphoric acid is heated for 4 h at 120° C. with stirring. The mixture is then treated, at ambient temperature, with a mixture of water and ice (500 ml and 500 g) and is then neutralized using 30% sodium hydroxide solution (pH>10). The insoluble material is collected by filtration, washed with water and dried at 60° C. 14.4 g of product are obtained.

Melting point: 189°–190° C.

Example 13 (Compound No. 17)

N,N-Dimethyl-8-(4-fluorophenyl)-4,5-dihydroimidazo[1,2-a]pyrrolo[ 1,2,3-cd]benzimidazole-9-acetamide.

13.1. 8-(4-Fluorophenyl)-α-hydroxy-N,N-dimethyl-4,5-dihydroimidazo[ 1,2-a]pyrrolo[1,2,3-cd]benzimidazole-9-acetamide.

27.2 g (0.155 mol) of 2,2-diethoxy-N,N-dimethylacetamide and 3 ml of concentrated hydrochloric acid in 250 ml of acetic acid are heated for 2 h, under a nitrogen atmosphere, at a temperature of 40° C. 12.7 g (0.155 mol) of sodium acetate are added thereto and heating is carried out for a further 15 min at 40° C. 14.3 g (0.0516 mol) of 8-(4-fluorophenyl)-4,5-dihydroimidazo[1,2-a]pyrrolo[1,2,3-cd]benzimidazole are added to this mixture, heating is maintained at 40° C. for 4 h and the reaction mixture is left standing overnight.

The acetic acid is evaporated under reduced pressure at a temperature of less than 45° C., the residue is treated with 250 ml of dichloromethane and a 10% aqueous sodium carbonate solution is added dropwise to alkaline pH.

The organic phase is separated by settling and dried over magnesium sulphate, the solvent is evaporated under reduced pressure and the crystalline residue is triturated in a 50/50 pentane/diethyl ether mixture. 17.5 g of product are obtained.

Melting point: 197°–198° C.

13.2. N,N-Dimethyl-8-(4-fluorophenyl)-4,5-dihydroimidazo[ 1,2-a]pyrrolo[1,2,3-cd]benzimidazole-9-acetamide.

13.2.1. α-Chloro-N,N-dimethyl-8-(4-fluorophenyl)-4,5-dihydroimidazo[ 1,2-a]pyrrolo[1,2,3-cd]benzimidazole-9-acetamide.

50 ml (≈0.7 mol) of thionyl chloride are added dropwise to a solution of 17.3 g (0.0457 mol) of 8-(4-fluorophenyl)-α-hydroxy-N,N-dimethyl-4,5-dihydroimidazo[ 1,2-a]pyrrolo[1,2,3-cd]benzimidazole-9-acetamide in 500 ml of dichloromethane and the mixture is stirred for 8 h at ambient temperature.

The mixture is evaporated under reduced pressure, the residue is taken up in toluene and the toluene is evaporated. The residue is triturated in diethyl ether, filtered off, washed with diethyl ether and dried. 19.2 g of product are obtained.

Melting point: 180°–185° C. (decomposition).

13.2.2. N,N-Dimethyl-8-(4-fluorophenyl)-4,5-dihydroimidazo[ 1,2-a]pyrrolo[1,2,3-cd]benzimidazole-9-acetamide.

27 g (0.175 mol) of Rongalite® are added to a solution, stirred under a nitrogen atmosphere, of 19 g (0.0438 mol) of a-chloro-N,N-dimethyl-8-(4-fluorophenyl)-4,5-dihydroimidazo[1,2-a]pyrrolo-[1,2,3cd]benzimidazole-9-acetamide in 500 ml of dichloromethane and the mixture is stirred at ambient temperature for 20 h. 200 ml of saturated aqueous sodium hydrogencarbonate solution are added, the organic phase is separated, washed with water, dried over magnesium sulphate and filtered, the solvent is evaporated under reduced pressure and the residue is purified by chromatography on a column of silica gel, elution being carried out with a 95/5 dichloromethane/methanol mixture. After recrystallization from 2-methoxyethanol, washing with ethanol, washing with diethyl ether and drying, 10.6 g of product are obtained.

Melting point: 259°–260° C.

Example 14 (Compound No. 18)

8-(4-Fluorophenyl)-4,5-dihydroimidazo[1,2-a]pyrrolo[1,2,3-cd]benzimidazole-9-acetic acid.

A mixture of 4 g (0.011 mol) of N,N-dimethyl-8-(4-fluorophenyl)-4,5-dihydroimidazo[1,2-a]pyrrolo[1,2,3-cd]benzimidazole-9-acetamide, 2.2 g (≈0.055 mol) of sodium hydroxide, 15 ml of water and 100 ml of 2-methoxyethanol is heated under a nitrogen atmosphere for 8 h at the reflux temperature.

The solvents are evaporated, the residue is taken up in 250 ml of water, an insoluble material is removed by filtration, acetic acid is added to the filtrate to pH=5 and the solid is collected by filtration, washed three times with water and dried. 3.5 g of product are obtained.

Melting point: 225°–227° C.

Example 15 (Compound No. 19)

8-(4-Fluorophenyl)-N-methyl-4,5-dihydroimidazo[1,2-a]pyrrolo[1,2,3-cd]benzimidazole-9-acetamide.

A mixture of 3.3 g (0.00984 mol) of 8-(4-fluorophenyl)-4,5-dihydroimidazo[1,2-a]pyrrolo[1,2,3-cd]benzimidazole-9-acetic acid, 1.95 g (0.012 mol) of N,N'-carbonyldiimidazole and 200 ml of dry tetrahydrofuran is heated under a nitrogen atmosphere at 50° C. for 4 h.

A stream of dry gaseous methylamine is then passed, while cold, into the mixture for 30 min, stirring is carried out for 2 h and the mixture is left standing overnight.

The mixture is evaporated under reduced pressure, the residue is taken up in 100 ml of water and the solid is separated by filtration, washed with water, dried and purified by chromatography on a column of silica gel, elution being carried out with a 97/3 dichloromethane/methanol mixture, and then by recrystallization from an 80/20 ethanol/2-methoxyethanol mixture. Finally, 1.6 g of product are obtained.

Melting point: 265°–266° C.

The chemical structures and the physical properties of several compounds according to the invention are illustrated in the following table.

TABLE (I)

| No. | n | X | R | Salt | M.p. (°C.) |
|---|---|---|---|---|---|
| 1 | 1 | H | H | — | 192–193 |
| 2 | 1 | H | —$CH_2CON(CH_3)_2$ | — | 224–225 |
| 3 | 1 | H | —$CH_2COOH$ | — | 270–275 (d) |
| 4 | 1 | H | —$CH_2COOCH_3$ | — | 164–165 |
| 5 | 1 | H | —$CH_2CONHCH_3$ | — | 269–270 |
| 6 | 2 | H | H | — | 103–104 |
|   |   |   |   | HCl | 295–300 (d) |
| 7 | 2 | H | —$CH_2CON(CH_3)_2$ | — | 216–217 |
| 8 | 2 | H | —$CH_2COOH$ | — | 246–248 (d) |
| 9 | 2 | H | —$CH_2CONH_2$ | — | 249–250 |
| 10 | 2 | H | —$CH_2CONHCH_3$ | — | 247–248 |
| 11 | 2 | H | —$CH_2COOCH_3$ | — | 123–124 |
| 12 | 1 | 3-F | H | — | 169–170 |
| 13 | 1 | 3-F | —$CH_2CON(CH_3)_2$ | — | 222–224 |
| 14 | 1 | 3-F | —$CH_2COOH$ | — | 274–277 (d) |
| 15 | 1 | 3-F | —$CH_2CONHCH_3$ | — | 296–297 |
| 16 | 1 | 4-F | H | — | 189–190 |
| 17 | 1 | 4-F | —$CH_2CON(CH_3)_2$ | — | 259–260 |
| 18 | 1 | 4-F | —$CH_2COOH$ | — | 225–227 |
| 19 | 1 | 4-F | —$CH_2CONHCH_3$ | — | 265–266 |
| 20 | 1 | 4-F | —$CH_2CONHCH_2CH_3$ | — | 267–268 (d) |
| 21 | 1 | 4-F | —$CH_2CONHCH_2CH_2CH_3$ | — | 256–257 (d) |
| 22 | 1 | 4-Cl | H | — | 209–210 |
| 23 | 1 | 4-Cl | —$CH_2CON(CH_3)_2$ | — | 277–278 |
| 24 | 1 | 4-Cl | —$CH_2COOH$ | — | 253 |

TABLE-continued (I)

| No. | n | X | R | Salt | M.p. (°C.) |
|---|---|---|---|---|---|
| 25 | 1 | 4-Cl | —CH$_2$CONHCH$_3$ | — | 289–290 |
| 26 | 1 | 4-CH$_3$ | H | — | 205–207 |
| 27 | 1 | 4-CH$_3$ | —CH$_2$CON(CH$_3$)$_2$ | — | 243–244 |
| 28 | 1 | 4-CH$_3$ | —CH$_2$COOH | — | 280–285 (d) |
| 29 | 1 | 4-CH$_3$ | —CH$_2$CONHCH$_3$ | — | 279–280 |
| 30 | 1 | 4-OCH$_3$ | H | — | 209–210 |
| 31 | 1 | 4-OCH$_3$ | —CH$_2$CON(CH$_3$)$_2$ | — | 216–217 |
| 32 | 1 | 4-OCH$_3$ | —CH$_2$COOH | — | 223–225 (d) |
| 33 | 1 | 4-OCH$_3$ | —CH$_2$CONHCH$_3$ | — | 266–267 (d) |
| 34 | 1 | 4-OH | —CH$_2$CON(CH$_3$)$_2$ | — | 259–260 |
| 35 | 1 | 4-OH | —CH$_2$CONHCH$_3$ | — | 308–310 |
| 36 | 1 | 3-F, 4-OCH$_3$ | H | — | 209–211 |
| 37 | 1 | 3-F, 4-OCH$_3$ | —CH$_2$CON(CH$_3$)$_2$ | — | 235–237 |
| 38 | 1 | 3-F, 4-OCH$_3$ | —CH$_2$COOH | — | >250 (d) |
| 39 | 1 | 3-F, 4-OCH$_3$ | —CH$_2$CONHCH$_3$ | — | 268–270 (d) |

Legend: in the "Salt" column, "-" denotes a compound in the base form and "HCl" denotes a hydrochloride; in the "M.p. (°C.)" column, "(d)" denotes a melting point with decomposition.

The compounds of the invention have been subjected to pharmacological tests which have demonstrated their advantage as substances possessing therapeutic activities.

Study of the membrane bindings with respect to $\omega_1$ (type-1-benzodiazepine) and $\omega_2$ (type-2 benzodiazepine) receptors.

The affinity of the compounds for the $\omega_1$ receptors of the cerebellum and the $\omega_2$ of the spinal cord was determined according to a variant of the method described by S. Z. Langer and S. Arbilla in Fund. Clin. Pharmacol., 2, 159–170 (1988), with use of $^3$H-flumazenil in place of $^3$H-diazepam as radioligand. The tissue of the cerebellum or of the spinal cord is homogenized for 60 s in 120 or 30 volumes, respectively, of ice-cold buffer (50 mM Tris/HCl, pH 7.4, 120 mM NaCl, 5 mM KCl) and then, after dilution to 1/3, the suspension is incubated with $^3$H-flumazenil (specific activity 78 Ci/mmol, New England Nuclear) at a concentration of 1 nM and with the compounds of the invention at various concentrations, in a final volume of 525 µl. After incubating for 30 minutes at 0° C., the samples are filtered under vacuum through Whatman GF/B® filters and they are washed immediately with ice-cold buffer. The specific binding of the $^3$H-flumazenil is determined in the presence of 1 µM unlabelled diazepam. The data are analysed according to the usual methods and the concentration IC$_{50}$, the concentration which inhibits the binding of the $^3$H-flumazenil by 50%, is calculated.

The IC$_{50}$ values of the compounds of the invention lie, in these tests, between 1 and 1000 nM.

Study of the anticonvulsant activity Activity with respect to clonic convulsions induced in rats by injection of pentetrazole The protocol of this test is a modification of that described by E. A. Swinyard and J. H. Woodhead in Antiepileptic Drugs, Raven Press, New York, 111–126 (1982).

The products to be tested are administered to the animals intraperitoneally 30 minutes before an intravenous injection of a dose of 20 mg/kg of pentetrazole. Immediately after the injection, the number of animals exhibiting clonic convulsions is recorded over 5 minutes.

The results are expressed by the AD$_{50}$, the dose which protects 50% of the animals, calculated according to the method of J. T. Lichtfield and F. Wilcoxon (J. Pharm. Exp. Ther., 96, 99–113 (1949)) from 3 or 4 doses, each administered to a group of 8 to 10 mice.

The AD$_{50}$ values of the compounds of the invention lie, in this test, between 0.5 and 10 mg/kg intraperitoneally.

Study of the anticonvulsant activity Activity with respect to convulsions induced in mice by isoniazid The intrinsic activity of the compounds is determined by the latent period for appearance of the convulsions induced by the subcutaneous administration of isoniazid (800 mg/kg) simultaneously with the compound to be tested, injected intraperitoneally, according to the protocol described by G. Perrault, E. Morel, D. Sanger and B. Zivkovic in Eur. J. Pharmacol., 156, 189–196 (1988). The results are expressed by the AD$_{50}$, the dose which produces 50% of the maximum effect, with respect to the control animals, determined from 3 or 4 doses, each administered to a group of 8 to 10 mice.

The AD$_{50}$ values of the compounds of the invention lie, in this test, between 1 and 100 mg/kg intraperitoneally and, depending on the compounds, the maximum effect can range up to 350%.

Study of the anxiolytic activity

The anxiolytic activity is evaluated in rats in the drink-intake conflict test, according to the method described by J. R. Vogel, B. Beer and D. E. Clody in Psychopharmacologia (Berl.), 21, 1–7 (1971).

After a water diet for 48 h, the rat is placed in a soundproof chamber equipped with a water pipette connected to an anxiometer delivering a slight electric shock every 20 licks. The number of shocks received is automatically counted for 3 minutes and makes it possible to evaluate the anxiolytic activity of the tested compounds. The results are expressed by the minimum effective dose (MED), the dose which produces a significant increase in the number of shocks received, with respect to the number observed in the control animals.

The MED values of the compounds of the invention lie, in this test, between 1 and 50 mg/kg intraperitoneally or orally.

Study of the hypnotic activity

The sedative or hypnotic activity of the compounds was determined by the observation of their effect on the electrocorticogram of rats, according to the method described by H. Depoortere, Rev. E.E.G. Neurophysiol., 10, 3, 207–214 (1980) and by H. Depoortere and M. Decobert, J. Pharmacol. (Paris), 14, 2, 195–265 (1983).

The products to be studied were administered intraperitoneally at increasing doses. They induce signs of sleep at doses ranging from 1 to 30 mg/kg.

The results of the tests carried out on the compounds of the invention show that, in vitro, they displace $^3$H-flumazenil from its specific binding sites in the cerebellum and spinal cord; consequently, they have an affinity for the $\omega_1$ and $\omega_2$ (type-1 and type-2 benzodiazepine) sites situated in the $GABA_A$-$\omega$ modulating sites-chloride channel macromolecular complex. They behave in vivo as complete or partial agonists with respect to these receptors.

They have hypnotic, anxiolytic and anticonvulsant properties and, consequently, can be used for treating conditions related to disorders of GABAergic transmission, such as anxiety, sleep disorders, epilepsy, spasticity, muscular contractions, cognitive disorders, withdrawal disorders with respect to alcoholism, and the like.

To this end, they can be presented in any pharmaceutical dosage form, in combination with appropriate excipients, for enteral or parenteral administration, for example in the form of tablets, dragées, capsules, including hard gelatin capsules, solutions or suspensions to be taken orally or by injection, suppositories and the like, containing doses which make possible the daily administration of 1 to 1000 mg of active substance.

The present invention provides a compound of the invention or a pharmaceutically acceptable salt thereof for use in the treatment of the human or animal body.

The present invention further provides a compound of the present invention or a pharmaceutically acceptable salt thereof for use in the treatment of disorders of GABAergic transmission.

The present invention provides a compound of the present invention or a pharmaceutically acceptable salt thereof in the manufacture of a medicament for the treatment of disorders of GABAergic transmission.

The compounds of the present invention or pharmaceutically acceptable salts thereof can be used in a method of treating or preventing disorders of GABAergic transmission in a subject which comprises administering to that subject an effective amount of a compound of the present invention or a pharmaceutically acceptable salt thereof.

We claim:

1. A compound of formula (I)

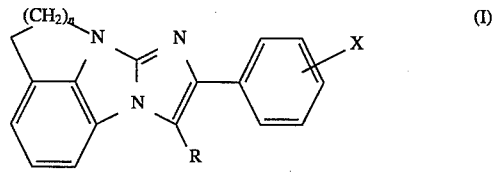

in which n represents the number 1 or 2,

X represents a hydrogen atom or indicates that the phenyl ring to which it is attached is substituted by one or two substituents independently chosen from halogen, $C_1$–$C_3$ alkyl, $C_1$–$C_3$ alkoxy and hydroxyl, and R represents a hydrogen atom, a group of formula —$CH_2$—$CO_2$—$R_1$, in which $R_1$ represents a hydrogen atom or a $C_1$–$C_6$ alkyl group; or a group of formula —$CH_2$—CO—$NR_2R_3$, in which each of $R_2$ and $R_3$ is independently a hydrogen atom or a $C_1$–$C_3$ alkyl group, or a pharmaceutically acceptable salt thereof.

2. A compound according to claim 1, or a pharmaceutically acceptable salt thereof, in which n represents the number 1, X represents a fluorine or chlorine atom, or a methyl or a methoxy group, and R represents a group of formula —$CH_2$—CO—NH—$CH_3$ or —$CH_2$—CO—$N(CH_3)_2$.

3. 8-(4-Fluorophenyl)-N-methyl-4,5-dihydroimidazo[1,2-a]-pyrrolo[1,2,3-cd]benzimidazole-9-acetamide or a pharmaceutically acceptable salt thereof.

4. A pharmaceutical composition which comprises a compound as defined in claim 1, or a pharmaceutically acceptable salt thereof, in combination with an excipient.

5. A method of treating or preventing disorders of GABAergic transmission in a subject which comprises administering to that subject an effective amount of a compound as defined in claim 1, or a pharmaceutically acceptable salt thereof.

* * * * *